US011510976B2

(12) United States Patent
Song

(10) Patent No.: US 11,510,976 B2
(45) Date of Patent: Nov. 29, 2022

(54) H7 AVIAN INFLUENZA VACCINE STRAIN WHICH DIFFERENTIATES INFECTED FROM VACCINATED ANIMALS, PREPARATION METHOD THEREFOR, AND APPLICATION

(71) Applicant: Zhejiang Difference Biological Technology Co., Ltd., Zhejiang (CN)

(72) Inventor: Jiasheng Song, Hangzhou (CN)

(73) Assignee: Zhejiang Difference Biological Technology Co., Ltd, Zhejiang (CN)

(*) Notice: Subject to any disclaimer, the term of this patent is extended or adjusted under 35 U.S.C. 154(b) by 0 days.

(21) Appl. No.: 16/766,048

(22) PCT Filed: Jun. 1, 2018

(86) PCT No.: PCT/CN2018/089525
§ 371 (c)(1),
(2) Date: May 21, 2020

(87) PCT Pub. No.: WO2019/100687
PCT Pub. Date: May 31, 2019

(65) Prior Publication Data

US 2020/0360508 A1 Nov. 19, 2020

(30) Foreign Application Priority Data

Nov. 21, 2017 (CN) ......................... 201711168682.7

(51) Int. Cl.
*A61K 39/145* (2006.01)
*C12N 15/87* (2006.01)
*A61K 39/00* (2006.01)

(52) U.S. Cl.
CPC ............ *A61K 39/145* (2013.01); *C12N 15/87* (2013.01); *A61K 2039/5252* (2013.01); *A61K 2039/552* (2013.01); *C12N 2760/16221* (2013.01); *C12N 2760/16222* (2013.01); *C12N 2760/16234* (2013.01)

(58) Field of Classification Search
None
See application file for complete search history.

(56) References Cited

FOREIGN PATENT DOCUMENTS

| | | |
|---|---|---|
| CN | 101365479 A | 2/2009 |
| CN | 102149405 A | 8/2011 |
| CN | 105338999 A | 2/2016 |
| CN | 105722976 A | 6/2016 |
| CN | 108018300 A | 5/2018 |

OTHER PUBLICATIONS

Flandorfer et al., Chimeric Influenza A Viruses with a Functional Influenza B Virus Neuraminidase or Hemagglutinin, 2003, Journal of Virology, vol. 77, No. 17, pp. 9116-9123.*
Muster, Thomas, et al.; “An Influenza A Virus Containing Influenza B Virus 5' and 3' Noncoding Regions on the Neuraminidase Gene is Attenuated in Mice”; Proc. Natl. Acad. Sci.; vol. 88; Jun. 1991; 5 pages.
Mitnaul, Lyndon, J., et al.; “Balanced Hemagglutinin and Neuraminidase Activities Are Critical for Efficient Replication of Influenza A Virus”; Journal of Virology; vol. 74, No. 13; Jul. 2000; 6 pages.
Flandorfer, Astrid, et al.; “Chimeric Influenza A Viruses with a Functional Influenza B Virus Neuraminidase or Hemagglutinin”; Journal of Virology; vol. 77, No. 17; Sep. 2003; 9 pages.
Nobusawa, E., et al.; “Comparison of Complete Amino Acid Sequences and Receptor-Binding Properties among 13 Serotypesof Hemagglutinins of Influenza A Viruses”; Virology; vol. 182; 1991; 11 pages.
Zhang, Jin, et al.; “Construction and Expression of RNase-Resisting His-Tagged Virus-Like Particles Containing FluA/B mRNA”; Chinese Journal of Virology; vol. 31, No. 6; Nov. 30, 2015; 5 pages.
Zheng, Wei, et al.; “Enhanced Growth of the H5N1 Influenza Vaccine Strain NIBRG-14 by the Neuraminidase’s Packaging Signal Sequence of A/ Puerto Rico/ 8/ 34”; Journal of University of Science and Technology of China; vol. 40, No. 4; Apr. 2010; 8 pages.
Wagner, Ralf, et al.; “Functional Balance Between Haemagglutinin and Neuraminidase in Influenza Virus Infections”; Rev. Med. Virol.; vol. 12; 2002; 8 pages.
Murakami, Shin, et al.; “Growth Determinants for H5N1 Influenza Vaccine Seed Viruses in MDCK Cells”; Journal of Virology; vol. 82, No. 21; Nov. 2008; 9 pages.
Rudneva, I. A., et al.; “Influenza A Virus Reassortants with Surface Glycoprotein Genes of the Avian Parent Viruses: Effects of HA and NA Gene Combinations on Virus Aggregation”; Archives of Virology; vol. 133; 1993; 14 pages.
Air, Gillian M.; “Sequence Relationships Among the Hemagglutinin Genes of 12 Subtypes of Influenza A Virus”; Proc. Natl. Acad. Sci.; vol. 78, No. 12; Dec. 1981; 5 pages.
PCT International Search Report and Written Opinion of the International Searching Authority; PCT/CN2018/089525; dated Aug. 29, 2018; 16 pages.

* cited by examiner

*Primary Examiner* — Benjamin P Blumel

(57) ABSTRACT

An H7 avian influenza vaccine strain which differentiates infected from vaccinated animals, a preparation method therefor, and an application. The highly pathogenic H7 avian influenza not only brings about huge economic losses to the livestock industry, but also seriously threatens public health safety. Conventional H7 avian influenza whole virus inactivated vaccines do have advantages such as being reliable in terms of effect, low in terms of cost and wide in terms of application range, but cannot serologically differentiate infected from vaccinated animals. The present invention uses NA of influenza B as a label to establish a method for constructing an H7 avian influenza vaccine strain which differentiates infection from vaccination, and may be used for the prevention, control and decontamination of the H7 avian influenza.

9 Claims, 2 Drawing Sheets

Specification includes a Sequence Listing.

SEQUENCE LISTING

```
<160> NUMBER OF SEQ ID NOS: 10

<210> SEQ ID NO 1
<211> LENGTH: 407
<212> TYPE: PRT
<213> ORGANISM: Artificial Sequence
<220> FEATURE:
<223> OTHER INFORMATION: an extracellular region amino acid sequence

<400> SEQUENCE: 1

Val Gln Ala Val Asn His Ser Ala Ala Lys Gly Val Thr Leu Leu Leu
1               5                   10                  15

Pro Glu Pro Glu Trp Thr Tyr Pro Arg Leu Ser Cys Pro Gly Ser Thr
            20                  25                  30

Phe Gln Lys Ala Leu Leu Ile Ser Pro His Arg Phe Gly Glu Ile Lys
        35                  40                  45

Gly Asn Ser Ala Pro Leu Ile Ile Arg Glu Pro Phe Ile Ala Cys Gly
    50                  55                  60

Pro Thr Glu Cys Lys His Phe Ala Leu Thr His Tyr Ala Ala Gln Pro
65                  70                  75                  80

Gly Gly Tyr Tyr Asn Gly Thr Arg Glu Asp Arg Asn Lys Leu Arg His
                85                  90                  95

Leu Ile Ser Val Lys Leu Gly Lys Ile Pro Thr Val Glu Asn Ser Ile
            100                 105                 110

Phe His Met Ala Ala Trp Ser Gly Ser Ala Cys His Asp Gly Lys Glu
        115                 120                 125

Trp Thr Tyr Ile Gly Val Asp Gly Pro Asp Ser Asn Ala Leu Leu Lys
    130                 135                 140

Ile Lys Tyr Gly Glu Ala Tyr Thr Asp Thr Tyr His Ser Tyr Ala Lys
145                 150                 155                 160

Asn Ile Leu Arg Thr Gln Glu Ser Ala Cys Asn Cys Ile Gly Gly Asp
                165                 170                 175

Cys Tyr Leu Met Ile Thr Asp Gly Pro Ala Ser Gly Val Ser Glu Cys
            180                 185                 190

Arg Phe Leu Lys Ile Arg Glu Gly Arg Ile Ile Lys Glu Ile Phe Pro
        195                 200                 205

Thr Gly Arg Val Lys His Thr Glu Glu Cys Thr Cys Gly Phe Ala Ser
    210                 215                 220

Asn Lys Thr Ile Glu Cys Ala Cys Arg Asp Asn Arg Tyr Thr Ala Lys
225                 230                 235                 240

Arg Pro Phe Val Lys Leu Asn Val Glu Thr Asp Thr Ala Glu Ile Arg
                245                 250                 255

Leu Met Cys Thr Glu Thr Tyr Leu Asp Thr Pro Arg Pro Asn Asp Gly
            260                 265                 270

Ser Ile Thr Gly Pro Cys Glu Ser Asp Gly Asp Lys Gly Ser Gly Gly
        275                 280                 285

Ile Lys Gly Gly Phe Val His Gln Arg Met Ala Ser Lys Ile Gly Arg
    290                 295                 300

Trp Tyr Ser Arg Thr Met Ser Lys Thr Lys Arg Met Gly Met Gly Leu
305                 310                 315                 320

Tyr Val Lys Tyr Asp Gly Asp Pro Trp Thr Asp Ser Glu Ala Leu Ala
                325                 330                 335

Leu Ser Gly Val Met Val Ser Met Glu Glu Pro Gly Trp Tyr Ser Phe
            340                 345                 350

Gly Phe Glu Ile Lys Asp Lys Lys Cys Asp Val Pro Cys Ile Gly Ile
```

-continued

```
        355                 360                 365

Glu Met Val His Asp Gly Gly Lys Thr Thr Trp His Ser Ala Ala Thr
    370                 375                 380

Ala Ile Tyr Cys Leu Met Gly Ser Gly Gln Leu Leu Trp Asp Thr Val
385                 390                 395                 400

Thr Gly Val Asp Met Ala Leu
                405


<210> SEQ ID NO 2
<211> LENGTH: 1224
<212> TYPE: DNA
<213> ORGANISM: Artificial Sequence
<220> FEATURE:
<223> OTHER INFORMATION: the sequence containing type B NA extracellular
      region

<400> SEQUENCE: 2

gttcaggctg taaatcattc tgcagcaaaa ggggtgacac ttcttctccc agaaccggaa     60

tggacatacc ctcgtttatc ttgcccgggc tcaacctttc agaaagcact cctaattagc    120

ccccatagat tcggagaaat caaaggaaac tcagctccct tgataataag ggaacctttt    180

attgcttgtg gaccaacgga atgcaaacac tttgctctaa cccattatgc agctcaacca    240

gggggatact acaatggaac aagagaagac agaaacaagc tgaggcatct aatttcagtc    300

aaattgggca aaatcccaac agtagaaaac tccattttcc acatggcagc ttggagcggg    360

tccgcatgcc atgatggtaa agaatggaca tatatcggag ttgatggccc cgacagtaat    420

gcattgctca aaataaaata tggagaagca tatactgaca cataccattc ctatgcaaaa    480

aacatcctaa ggacacaaga aagtgcctgc aattgcatcg gggagattg ttatcttatg    540

ataactgatg gcccagcttc aggggttagt gaatgcagat tccttaagat tcgagagggc    600

agaataataa aagaaatatt tccaacagga agagtaaaac atactgagga atgcacatgc    660

ggatttgcca gcaacaaaac catagaatgt gcttgtagag ataaccgtta cacagcaaaa    720

agaccctttg tcaaattaaa tgtggagact gatacagcgg aaataagatt gatgtgcaca    780

gagacttatt tggacacccc cagaccaaat gatggaagca taacagggcc ttgcgaatct    840

gatggggaca aagggagtgg aggcatcaag ggaggatttg ttcatcaaag aatggcatcc    900

aagattggaa ggtggtactc tcgaacgatg tctaaaacca aaagaatggg gatgggactg    960

tatgtaaaat atgatggaga cccatggact gacagtgaag cccttgctct tagtggagta   1020

atggtttcaa tggaagaacc tggttggtat tcctttggct tcgaaataaa agataagaaa   1080

tgtgatgtcc cctgtattgg gatagaaatg gtacatgatg gtgggaaaac gacttggcac   1140

tcagcagcaa cagccattta ttgtttaatg ggctcaggac aattgctgtg ggacactgtc   1200

acaggtgttg atatggctct gtaa                                          1224


<210> SEQ ID NO 3
<211> LENGTH: 203
<212> TYPE: DNA
<213> ORGANISM: Artificial Sequence
<220> FEATURE:
<223> OTHER INFORMATION: 5'-end packaging signal sequence

<400> SEQUENCE: 3

agcaaaagca ggggtttaaa atgaatccaa atcagaaaat aataaccatt ggatcaatct     60

gtctggtagt cggactaatt agcctaatat tgcaaatagg gaatataatc tcaatatgga    120

ttagccattc aattcaaact ggaagtcaaa accatactgg aatatgcaac caaaacatca    180
```

```
ttacctataa aaatagcacc tgg                                           203


<210> SEQ ID NO 4
<211> LENGTH: 185
<212> TYPE: DNA
<213> ORGANISM: Artificial Sequence
<220> FEATURE:
<223> OTHER INFORMATION: 3'-end packaging signal sequence

<400> SEQUENCE: 4

gaggccgtgc ttctgggttg aattaatcag gggacgacct aaagaaaaaa caatctggac     60

tagtgcgagc agcatttctt tttgtggcgt gaatagtgat actgtagatt ggtcttggcc    120

agacggtgct gagttgccat tcagcattga caagtagtct gttcaaaaaa ctccttgttt    180

ctact                                                                185


<210> SEQ ID NO 5
<211> LENGTH: 890
<212> TYPE: DNA
<213> ORGANISM: Artificial Sequence
<220> FEATURE:
<223> OTHER INFORMATION: the nucleotide sequence of DeltaNS

<400> SEQUENCE: 5

agcaaaagca gggtgacaaa aacataatgg atccaaacac tgtgtcaagc tttcaggtag     60

attgctttct ttggcatgtc cgcaaacgag ttgcagacca agaactaggc gatgccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcatgataat ggtccatgct catacccaag cagaaagtgg    360

caggccctct ttgtatcaga atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600

ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact               890


<210> SEQ ID NO 6
<211> LENGTH: 407
<212> TYPE: PRT
<213> ORGANISM: Artificial Sequence
<220> FEATURE:
<223> OTHER INFORMATION: the extracellular region protein amino acid
      sequence

<400> SEQUENCE: 6

Val Gln Ala Val Asn Arg Ser Ala Thr Lys Gly Val Thr Leu Leu Leu
1               5                   10                  15

Pro Glu Pro Glu Trp Thr Tyr Pro Arg Leu Ser Cys Pro Gly Ser Thr
            20                  25                  30

Phe Gln Lys Ala Leu Leu Ile Ser Pro His Arg Phe Gly Glu Thr Lys
```

-continued

```
        35                  40                  45

Gly Asn Ser Ala Pro Leu Ile Ile Arg Glu Pro Phe Ile Ala Cys Gly
    50                  55                  60

Pro Asn Glu Cys Lys His Phe Ala Leu Thr His Tyr Ala Ala Gln Pro
65                  70                  75                  80

Gly Gly Tyr Tyr Asn Gly Thr Arg Gly Asp Arg Asn Lys Leu Arg His
                85                  90                  95

Leu Ile Ser Val Lys Leu Gly Lys Ile Pro Thr Val Glu Asn Ser Ile
            100                 105                 110

Phe His Met Ala Ala Trp Ser Gly Ser Ala Cys His Asp Gly Lys Glu
        115                 120                 125

Trp Thr Tyr Ile Gly Val Asp Gly Pro Asp Asn Asn Ala Leu Leu Lys
    130                 135                 140

Val Lys Tyr Gly Glu Ala Tyr Thr Asp Thr Tyr His Ser Tyr Ala Asn
145                 150                 155                 160

Lys Ile Leu Arg Thr Gln Glu Ser Ala Cys Asn Cys Ile Gly Gly Asn
                165                 170                 175

Cys Tyr Leu Met Ile Thr Asp Gly Ser Ala Ser Gly Val Ser Glu Cys
            180                 185                 190

Arg Phe Leu Lys Ile Arg Glu Gly Arg Ile Ile Lys Glu Ile Phe Pro
        195                 200                 205

Thr Gly Arg Val Lys His Thr Glu Glu Cys Thr Cys Gly Phe Ala Ser
    210                 215                 220

Asn Lys Thr Ile Glu Cys Ala Cys Arg Asp Asn Ser Tyr Thr Ala Lys
225                 230                 235                 240

Arg Pro Phe Val Lys Leu Asn Val Glu Thr Asp Thr Ala Glu Ile Arg
                245                 250                 255

Leu Met Cys Thr Asp Thr Tyr Leu Asp Thr Pro Arg Pro Asn Asp Gly
            260                 265                 270

Ser Ile Thr Gly Pro Cys Glu Ser Asn Gly Asp Lys Gly Ser Gly Gly
        275                 280                 285

Ile Lys Gly Gly Phe Val His Gln Arg Met Glu Ser Lys Ile Gly Arg
    290                 295                 300

Trp Tyr Ser Arg Thr Met Ser Lys Thr Glu Arg Met Gly Met Gly Leu
305                 310                 315                 320

Tyr Val Lys Tyr Asp Gly Asp Pro Trp Ala Asp Ser Asp Ala Leu Ala
                325                 330                 335

Phe Ser Gly Val Met Val Ser Met Lys Glu Pro Gly Trp Tyr Ser Phe
            340                 345                 350

Gly Phe Glu Ile Lys Asp Lys Lys Cys Asp Val Pro Cys Ile Gly Ile
        355                 360                 365

Glu Met Val His Asp Gly Gly Lys Glu Thr Trp His Ser Ala Ala Thr
    370                 375                 380

Ala Ile Tyr Cys Leu Met Gly Ser Gly Gln Leu Leu Trp Asp Thr Val
385                 390                 395                 400

Thr Gly Val Asp Met Ala Leu
                405
```

<210> SEQ ID NO 7
<211> LENGTH: 1224
<212> TYPE: DNA
<213> ORGANISM: Artificial Sequence
<220> FEATURE:
<223> OTHER INFORMATION: the DNA sequence for coding the extracellular region protein amino acid sequence

<400> SEQUENCE: 7

```
gttcaggctg tgaaccgttc tgcaacaaaa ggggtgacac ttcttctccc agaaccggag     60
tggacatacc cgcgtttatc ttgcccgggc tcaacctttc agaaagcact cctaattagc    120
cctcatagat tcggagaaac caaaggaaac tcagctccct tgataataag ggaacctttt    180
attgcttgtg gaccaaatga atgcaaacac tttgctctaa cccattatgc agcccaacca    240
gggggatact acaatggaac aagaggagac agaaacaagc tgaggcatct aatttcagtc    300
aaattgggca aaatcccaac agtagaaaac tccattttcc acatggcagc atggagcggg    360
tccgcgtgcc atgatggtaa ggaatggaca tatatcggag ttgatggccc tgacaataat    420
gcattgctca aagtaaaata tggagaagca tatactgaca cataccattc ctatgcaaac    480
aaaatcctaa gaacacaaga aagtgcctgc aattgcatcg gggaaattg ttatcttatg     540
ataactgatg gctcagcttc aggtgttagt gaatgcagat ttcttaagat tcgagagggc    600
cgaataataa aagaaatatt tccaacagga agagtaaaac acactgagga atgcacatgc    660
ggatttgcca gcaataaaac catagaatgt gcctgtagag ataacagtta cacagcaaaa    720
agacctttg tcaaattaaa cgtggagact gatacagcag aaataagatt gatgtgcaca     780
gatacttatt tggacacccc cagaccaaac gatggaagca taacaggccc ttgtgaatct    840
aatggggaca aagggagtgg aggcatcaag ggaggatttg ttcatcaaag aatggaatcc    900
aagattggaa ggtggtactc tcgaacgatg tctaaaactg aaaggatggg gatgggactg    960
tatgtcaagt atgatggaga cccatgggct gacagtgatg ccctagcttt tagtggagta   1020
atggtttcaa tgaaagaacc tggttggtac tcctttggct tcgaaataaa agataagaaa   1080
tgcgatgtcc cctgtattgg gatagagatg gtacatgatg gtggaaaaga gacttggcac   1140
tcagcagcaa cagccattta ctgtttaatg ggctcaggac agctgctgtg ggacactgtc   1200
acaggtgttg acatggctct gtaa                                          1224
```

<210> SEQ ID NO 8
<211> LENGTH: 12
<212> TYPE: PRT
<213> ORGANISM: Artificial Sequence
<220> FEATURE:
<223> OTHER INFORMATION: wild type HA protein sequence

<400> SEQUENCE: 8

```
Val Pro Lys Gly Lys Arg Thr Ala Arg Gly Leu Phe
1               5                   10
```

<210> SEQ ID NO 9
<211> LENGTH: 10
<212> TYPE: PRT
<213> ORGANISM: Artificial Sequence
<220> FEATURE:
<223> OTHER INFORMATION: mutated wild type HA protein sequence 1

<400> SEQUENCE: 9

```
Val Pro Ser Ser Arg Ser Arg Gly Leu Phe
1               5                   10
```

<210> SEQ ID NO 10
<211> LENGTH: 8
<212> TYPE: PRT
<213> ORGANISM: Artificial Sequence
<220> FEATURE:
<223> OTHER INFORMATION: mutated wild type HA protein sequence 2

-continued

<400> SEQUENCE: 10

```
Val Pro Lys Gly Arg Gly Leu Phe
1               5
```

H7 AVIAN INFLUENZA VACCINE STRAIN WHICH DIFFERENTIATES INFECTED FROM VACCINATED ANIMALS, PREPARATION METHOD THEREFOR, AND APPLICATION

CROSS-REFERENCE TO RELATED APPLICATIONS

This application is a U.S. National Stage of International Patent Application No. PCT/CN2018/089525 filed on Jun. 1, 2018, which claims priority to Chinese Patent Application No. 201711168682.7 filed on Nov. 21, 2017, both of which are incorporated herein as if reproduced in their entireties.

INCORPORATION-BY-REFERENCE OF MATERIAL SUBMITTED AS A TEXT FILE VIA THE OFFICE ELECTRONIC FILING SYSTEM (EFS-WEB)

This application contains a Sequence Listing in ASCII text file format entitled, "GWPCTP201912561 ST25 Replacement Sequence Listing", created on Feb. 9, 2022, that is 14 KB. The GWPCTP201912561 ST25 Replacement Sequence Listing is incorporated by reference herein in its entirety.

TECHNICAL FIELD

The disclosure belongs to the field of genetic engineering vaccines, relates to a preparation method of an H7 avian influenza vaccine strain which differentiates infection from vaccination, and an application thereof.

BACKGROUND

Avian influenza virus belongs to the genus of influenza virus, the family of Orthomyxoviridae. Influenza viruses are classified into types A, B, and C in terms of antigenic diversity, wherein influenza A viruses have a broad species tropism (including avian, human, swine, etc.), with a strong pathogenicity and huge damages. Influenza B viruses are primarily limited to the human population, although rare infections of seals have been documented, with a relatively low pathogenicity. Influenza C viruses are only found in human and swine. The genomes of influenza A and B can be divided into 8 gene segments in total: PB2, PB1, PA, NP, HA, NA, M, and NS. Once being infected, hosts may generate a large amount of antibodies to HA, NA, M1 and NP proteins, wherein HA may induce major neutralizing antibodies directly. It is found in previous researches that the four major antibodies against HA, NA, M1 and NP induced by viruses of types A and B have no serological cross-reactivity. The antigenic diversity of the HA and NA proteins of the influenza virus is used to classify influenza viruses into different subtypes (HnNn), wherein there are 18 subtypes for HA and 11 subtypes for NA. The sequence homologies among different subtypes of HA proteins are between 40%-80% (Air G M. Proceedings of the National Academy of Sciences of the United States of America, 1981, 78(12):7639. Nobusawa E, et al. Virology, 1991, 182(2): 475-485). There are no subtypes for influenza B, with high similarities between each virus strain gene. According to the antigenic variant, influenza B viruses are currently divided into only two lineages, Victoria group (named following B/Victoria/2/1987) and Yamagata group (named following B/Yamagata/16/1988) respectively. There are almost all subtypes of influenza A in avian species, playing important roles in the storage and evolution of the virus. The global epidemic of avian influenza has caused huge economic losses to the poultry industry, the cases of human infections with avian influenza are increasing gradually with the gradual adaptation of avian influenza viruses to human. Compared with seasonal human influenza, human infections with avian influenza are characterized by severe morbidity and high mortality, greatly threatening the public health safety. In numerous subtypes of avian influenza, highly pathogenic H7 avian influenza is extremely hazardous, causing huge economic losses. Highly pathogenic H7 avian influenza may result in 100% death of the poultry in a few days, and may infect humans directly. Infections in humans are serious in symptoms and high in mortalities.

At present, vaccination is one of the most effective methods for preventing and controlling avian influenza. The vaccine strains constructed with the internal genes of the chick-embryo highly adaptable strain PR8 as the background with the external genes (HA, NA) which are substituted for the epidemic strains are safe, effective and inexpensive, being applied most extensively in China, and playing important roles in preventing and controlling avian influenza. However, this kind of whole virus inactivated vaccine cannot serologically differentiate infected from vaccinated animals, causing a great obstacle in the monitoring and decontamination of avian influenza virus. The HA protein attaches the virus to the cell surface by binding to sialic-acid-containing receptors and promotes viral penetration by mediating fusion of the endosomal and viral membranes, and the NA protein functions as a homotetramer, facilitating the mobility of virions by removing sialic acid residues from viral glycoproteins and infected cells during both entry and release from cells. Therefore, a balance of competent HA and NA (the matching of HA-NA) activities appears critical and may directly affect the replication capacities and growth properties of influenza viruses (Mitnaul L J, Matrosovich M N, Castrucci M R, et al. Balanced Hemagglutinin and Neuraminidase Activities Are Critical for Efficient Replication of Influenza A Virus[J]. Journal of Virology, 2000, 74(13):6015-20). Therefore, selection of viruses with HA and NA functional balance is one of the keys to develop excellent vaccine strains (Murakami S, et al. Growth Determinants for H5N1 Influenza Vaccine Seed Viruses in MDCK Cells[J]. Journal of Virology, 2008, 82(21):10502). For ensuring the functional balance between vaccine strains HA and NA, the two genes are generally derived from the same virus strain. Introduction of heterogeneous NAs may disrupt the functional balance between HA-NA, thus reducing the growth and replication capacities of viruses, even resulting in recombinant viruses unable to be rescued. In general, such risks would increase continually as the similarity of the introduced NA gene is reduced (compared with homogenous NAs). Replacements among different subtypes of NA would affect biological properties in terms of replication and growth, of the rescued recombinant viruses. This is also the reason why there are only a few advantageous subtype combinations in nature (e.g., common H9N2, H5N1, H7N9, etc.), rather than random combinations of HA-NA (e.g., rare H9N1, H5N9, etc.)(Wagner R et al, Functional balance between haemagglutinin and neuraminidase in influenza virus infections[J]. Reviews in Medical Virology, 2002, 12(3):159). Rudneva et al used different combinations of N1 genes and subtypes of HA gene to generate recombinant viruses, and found that the growth properties of the recombinant viruses of the rescued H3, H4, H10 and H13 on chick-embryos are poorer than their wild-type viruses (Rudneva I A et al. Influenza A virus reassortants with surface glycoprotein genes of the avian parent viruses: effects of HA and NA gene combinations on virus aggregation. [J]. Archives of Virology, 1993, 133(3-4):437-450). Due to the great difference of NA protein in types B and A influenza viruses (with the similarity <30%), the success probability of obtaining the A/B chimeric virus by introducing type B NA is small. Moreover, there may be defects in the growth properties of the rescued A/B NA chimeric viruses, and it may need to be adapted by serial passages in vitro. However, serial passages may bring the risk of antigenic variation, thus resulting in great differences between the antigenicity of the prepared vaccine strains and the original wild-type epidemic strains. So far, there have not been any reports of successful rescue for chimeric viruses containing type B NA.

Although the existing H7 whole virus inactivated vaccines do have advantages such as being reliable in terms of immune effect and low cost, the fact that they cannot serologically differentiate infected from vaccinated animals (DIVA) seriously affects monitoring on the virus epidemic, thus hindering the thoroughly decontamination of H7 avian influenza in the farms, causing a persistent risk to the public health and food safety. Therefore, it is needed currently to prepare a new H7 avian influenza vaccine strain which can differentiate infection from vaccination.

SUMMARY

To resolve the above issues, the application, firstly develops a preparation method of a new H7 avian influenza vaccine which differentiates infection from vaccination by introducing the NA gene of influenza B as a label. Moreover, in the present invention, through partial deletion of NS genes and weakening modification of HAs, the safety property of the rescued vaccine strains is obviously superior to that of the ordinary vaccine strains. Therefore, the present invention provides a preparation method of an H7 avian influenza vaccine which is safe and effective, low in production cost and can serologically differentiate infected from vaccinated animals, which has great application values and prominent public health significance.

The object of the present invention is to provide an H7 avian influenza vaccine strain which differentiates infection from vaccination and an application thereof.

Another object of the present invention is to provide a preparation method of an H7 avian influenza vaccine strain which differentiates infection from vaccination.

The technical solutions employed in the present invention are as below:

An application of a label gene sequence in the preparation of an H7 avian influenza vaccine strain which differentiates influenza A virus infection from vaccination, the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding the extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the H7 avian influenza vaccine strain further contains an H7 subtype HA gene encoding VPKGKRTARGLF (SEQ ID No. 8) or a mutated H7 subtype HA gene; wherein the mutated H7 subtype HA gene has been mutated to encode VPSSRSRGLF (SEQ ID No.: 9) or VPKGRGLF (SEQ ID NO. 10) in place of VPKGKRTARGLF (SEQ ID No. 8).

Furthermore, the influenza B virus includes influenza B viruses of Victoria group and Yamagata group.

Furthermore, the influenza B virus specifically includes, but not limited to, virus strains B/Massachusetts/2/2012, B/Brisbane/60/2008, B/Yamagata/16/1988, B/Malaysia/2506/04.

Furthermore, the label gene sequence further contains packaging signal sequences at its both ends, the packaging signal is a packaging signal of H1 subtype NA, or a packaging signal sequence having at least 80% homology, or at least 85% homology, or at least 90% homology, or at least 95% homology with the packaging signal of H1 subtype NA.

Furthermore, the label gene sequence further contains packaging signal sequences at its both ends, wherein the 5'-end packaging signal sequence includes the noncoding region sequence, the intracellular region sequence, and the transmembrane region sequence.

Furthermore, the intracellular region sequence encodes 5~7 amino acids, with the amino acid sequences within the cell.

Furthermore, the transmembrane region sequence encodes 24~32 amino acids, with the amino acid sequences in the transmembrane region.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the label gene sequence further contains packaging signal sequences at its both ends, wherein the 3'-end packaging signal sequence is SEQ ID NO:4, or a sequence having at least 80% homology, or at least 85% homology, or at least 90% homology, or at least 95% homology with SEQ ID NO:4.

A preparation method of an H7 avian influenza vaccine strain which differentiates influenza A virus infection from vaccination, including the following steps: the label gene sequence is rescued with an HA gene or a mutated H7 subtype HA gene of H7 avian influenza virus over a reverse genetic system to obtain a recombinant vaccine strain, that is an H7 avian influenza vaccine strain which differentiates influenza A virus infection from vaccination;

the mutated H7 subtype HA gene is capable of mutating the amino acid sequence VPKGKRTARGLF in the wild type HA protein into VPSSRSRGLF or VPKGRGLF;

the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding an extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the label gene sequence further contains packaging signal sequences at its both ends.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the 3'-end packaging signal sequence of the label gene sequence is SEQ ID NO:4, or a sequence having at least 80% homology, or at least 85% homology, or at least 90% homology, or at least 95% homology with SEQ ID NO:4.

Furthermore, there are additional 6 PR8 internal genes used during the rescue with the reverse genetic system which are ΔNS or wild type NS and PB2, PB1, PA, NP, M; wherein ΔNS is a mutated NS gene, the nucleotide sequence of ΔNS is as shown in SEQ ID NO:5.

An H7 avian influenza vaccine strain which differentiates influenza A virus infection from vaccination, which is named as H7 avian influenza vaccine candidate strain Re-Mu2H7-DIVA-ΔNS, has been preserved in China Center for Type Culture Collection, with the preservation number of CCTCC NO: V201742.

An application of the above described vaccine strain in the preparation of avian influenza vaccines.

The applicants have preserved the inventive vaccine strain Re-Mu2H7-DIVA-ΔNS in China Center for Type Culture Collection, the address of which is Wuhan University, China. The Collection Center received the vaccine strain provided by the applicants on Oct. 19, 2017. The preservation number of the culture issued by the Collection Center is CCTCC NO: V201742, the proposed classification name is H7 avian influenza vaccine candidate strain Re-Mu2H7-DIVA-ΔNS, the preserved vaccine strain has been identified as viable on Oct. 28, 2017.

The beneficial effects of the invention are:

(1) The application, firstly develops a preparation method of a new H7 avian influenza vaccine which differentiates infection from vaccination by introducing NA of influenza B gene as a label.

(2) The present invention has successfully constructed an H7 avian influenza vaccine strain which differentiates infected from vaccinated animals, in which the NA gene and HA gene exhibit good compatibility, showing good biological properties in terms of replication and growth, without in vitro passage adaptation, thus avoiding the antigenic variation that may be caused by the passage adaptation. Even when passages for the 3rd generation, it still remains low pathogenicity and high titer growth properties in chick-embryos. The present invention has great application values and prominent public health significance.

(3) The highly pathogenic H7 avian influenza not only brings about huge economic losses to the livestock industry, but also seriously threatens public health safety. Conventional H7 avian influenza whole virus inactivated vaccines do have effects, but cannot serologically differentiate antibodies produced from infection from those produced from vaccination, causing a great obstacle in the monitoring and decontamination of avian influenza. The present invention firstly has successfully constructed an H7 avian influenza vaccine strain which differentiates infection from vaccination by using NA of influenza B as a label, having great significance and application values in the prevention, control and decontamination of the H7 avian influenza.

DESCRIPTION OF THE EMBODIMENTS

The present invention will be illustrated in detail in conjunction with the following specific examples and the accompanying figures, and the embodiments of the invention are not limited to this. For unnoted conventional experimental methods, see "Guideline for Molecular Cloning", the 3rd edition (Sambrook, ed., Science press, 2002).

Example 1 A Preparation Method of Avian Influenza Vaccine Strain Re-MuH7-DIVA-ΔNS Virus (1) Construction of Low Pathogenic HA Mutant Gene The pFlu vector is a kind of bidirectional transcription vector, which may transcribe viral RNA by the human poll promoter, and also transcribe viral mRNA by CMV promoter, thus synthesizing the viral proteins (Hoffmann et al., PNAS, USA 97, 6108-6113, 2000).

Figure 2:
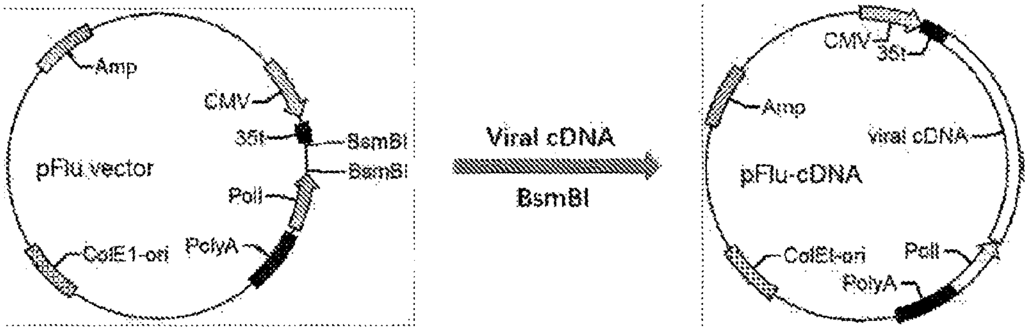
FIG. 2 is the pFLu vector map and the clone schematic diagram of influenza virus gene segments.

HA gene (KY855526) in the artificially synthesized wild type H7 avian influenza, of which the (KRTA) sequence in the highly pathogenic characteristic sequence (VPKGKRTARGLF) in this wild type HA amino acid sequence is deleted through site-directed mutagenesis to obtain the corresponding low pathogenic Mu1HA gene sequence; or the highly pathogenic characteristic sequence (VPKGKRTARGLF) is mutated into (VPSSRSRGLF) to obtain the corresponding low pathogenic Mu2HA gene sequence; the mutated Mu1HA, Mu2HA genes are cloned into the pFlu vector through a site to obtain the recombinant plasmid pFlu-Mu1HA and pFlu-Mu2HA, with the construction schematic diagram shown in FIG. 2.

(2) Construction of Low Pathogenic A/B Chimeric NA Gene

Figure 1:
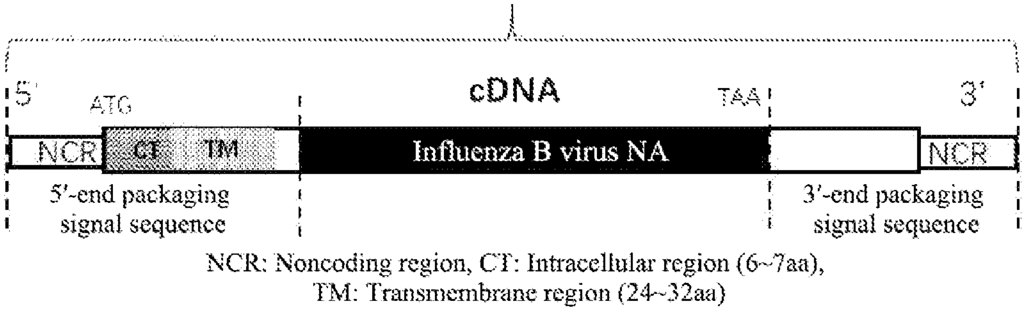
FIG. 1 is the structure schematic diagram of artificially synthesized A/B chimeric NA gene.

Constructing the artificially synthesized A/B chimeric NA gene as shown in FIG. 1, which contains a DNA sequence (SEQ ID NO: 2) for coding an extracellular region amino acid sequence (SEQ ID NO: 1) in influenza B virus NA as the label gene sequence, the sequence containing type B NA extracellular region as shown in SEQ ID NO: 2 deriving from B/Massachusetts/2/2012 in the influenza B virus Yamagata group (Ping J et al, PNAS, 2016, 113(51):E8296-E8305), the label gene sequence further contains packaging signal sequences at its both ends, wherein the 5'-end packaging signal sequence (SEQ ID NO:3) includes the noncoding region sequence, the intracellular region sequence and the transmembrane region sequence, the 3'-end packaging signal sequence is SEQ ID NO:4. The chimeric NA is inserted into the pFlu vector through the BsmBI site to obtain a recombinant plasmid pFlu-PR8-BNA.

(3) Acquisition of Re-MuH7-DIVA-ΔNS Vaccine Strain

For ensuring the safety property of the vaccine strain, the wild type virus NS1 gene is modified, the nucleotide sequence of the modified mutant gene ΔNS is as shown in SEQ ID NO:5. The virus containing the mutant gene ΔNS has lost the function of antagonizing interferons, thus only can grow and propagate in interferon-deficient cells or chick embryos with underdeveloped interferon systems, therefore having good safety property.

The recombinant vaccine strain Re-MuH7-DIVA-ΔNS is rescued with the classical "6+2" influenza reverse genetic system. Each 0.5 ug of 6PR8 internal genes pFlu-PR8-PB2, pFlu-PR8-PB1, pFlu-PR8-PA, pFlu-PR8-NP, pFlu-PR8-M, pFlu-PR8-ΔNS and 2 external genes pFlu-Mu1-HA/pFlu-Mu2-HA, pFlu-PR8-BNA are co-transfected into 293T cells (Lipofectamine 3000). 24 h after transfection, a culture medium containing TPCK-Trypsin at a final concentration of 0.5 ug/ml is exchanged, and 48 h after transfection, the cell supernatant is collected, which is inoculated into 8-day-old SPF chick embryos at 0.2 ml per embryo by allantoic cavity inoculation. After inoculation, chick embryos are cultured in an incubator at 37° C. for 48 h. The chick embryo allantoic fluid (F0 generation) is collected to obtain the vaccine strains Re-Mu1H7-DIVA-ΔNS and Re-Mu2H7-DIVA-ΔNS respectively, and it is determined whether they have hemagglutination titers. If they have no hemagglutination titers, the obtained viruses are blind passaged for one generation, and then determined whether they have hemagglutination titers.

Example 2 Growth Properties of Vaccine Strains Containing Different Low Pathogenic Modified Mutant Genes Mu1HA, Mu2HA on Chick Embryos The vaccine strains Re-Mu1H7-DIVA-ΔNS and Re-Mu2H7-DIVA-ΔNS obtained in Example 1 are serially passaged on 8-day-old SPF chick embryos (F0-F3) respectively. 48 hours after vaccination, each generation of viruses are harvested and determined their hemagglutination titers (HA titers).

The detection results are shown in Table 1, from which it can be seen that the growth properties of Re-Mu2H7-DIVA-ΔNS are obviously superior to those of Re-Mu1H7-DIVA-ΔNS. As the genetic backgrounds of Re-Mu1H7-DIVA-ΔNS and Re-Mu2H7-DIVA-ΔNS reassortant viruses are almost the same, only different in the modifications of the highly pathogenic wild type HA, therefore, the modification mode on Mu2-HA is more favorable for the growth of H7 avian influenza on chick embryos, reaching 5 log 2~6 log 2. No chick embryo deaths are observed during the passages, indicating that the recombinant viruses exhibit low pathogenic or no pathogenic on chick embryos, with good safety property. Taking F0 and F3-generation viruses of which the artificially synthesized A/B chimeric NA gene is amplified by RT-PCR, it is demonstrated by sequencing that chimeric NA gene can be stably passed to progeny viruses.

In conclusion, the rescued Re-Mu2H7-DIVA-ΔNS strains become ones with low pathogenicity or without pathogenicity, which only can grow and propagate in interferon-deficient cells or low-age chick embryos with underdeveloped interferon systems, therefore having good safety property. After incubation on 8-day-old SPF chick embryos for 48 hours, their HA titers may reach 6 log 2. Due to NS1 partial deletion of Re-Mu2H7-DIVA-ΔNS strain, its growth titer on chick embryos is lower than that of normal non-deleted viruses, but better than non-deleted wild type viruses in terms of safety.

TABLE 1

Growth properties of vaccine strains Re-Mu1H7-DIVA-ΔNS, Re-Mu2H7-DIVA-ΔNS with different low pathogenic modifications on chick embryos

| Passage | HA Titers (log2) | |
|---|---|---|
| Number | Re-Mu1H7-DIVA-ΔNS | Re-Mu2H7-DIVA-ΔNS |
| F0 | 0 | 5 |
| F1 | 2 | 6 |
| F2 | 3 | 6 |
| F3 | 3 | 6 |

The applicants have preserved the inventive vaccine strain Re-Mu2H7-DIVA-ΔNS in China Center for Type Culture Collection, the address of which is Wuhan University, China. The Collection Center received the vaccine strain provided by the applicants on Oct. 19, 2017. The preservation number of the culture issued by the Collection Center is CCTCC NO: V201742, the proposed classification name is H7 avian influenza vaccine candidate strain Re-Mu2H7-DIVA-ΔNS, the preserved vaccine strain has been identified as viable on Oct. 28, 2017.

Example 3 A Preparation Method of an H7 Avian Influenza Vaccine Strain Re-MuH7-DIVA-ΔNS which Differentiates Influenza a Virus Infection from Vaccination The preparation method of Example 3 is the same as that of Example 1, except that in constructing the artificially synthesized A/B chimeric NA gene as shown in FIG. 1, the DNA sequence for coding the extracellular region protein amino acid sequence in influenza B virus NA is different from that in Example 1, the remaining are all the same as Example 1.

In this Example, the DNA sequence for coding the extracellular region protein amino acid sequence (SEQ ID NO: 6) in influenza B virus NA is shown in SEQ ID NO: 7, which is used as the label gene sequence, the sequence shown in SEQ ID NO: 7 deriving from B/Brisbane/60/2008 of influenza B virus Victoria group (Ping J et al, PNAS, 2016, 113(51):E8296-E8305).

The Re-MuH7-DIVA-ΔNS vaccine strain prepared in the present invention will be further detected for its effects below.

Process: Re-Mu2H7-DIVA-ΔNS vaccine strain prepared in Example 1 (NA extracellular region gene is derived from B/Massachusetts/2/2012 of Yamagata group), Re-MuH7-DIVA-ΔNS vaccine strain prepared in Example 3 (NA extracellular region gene is derived from B/Brisbane/60/2008 of Victoria group), PR8-ΔNS virus (NS-deficient PR8 virus) of the control group 1, PR8-WT virus (wild type PR8 virus) of the control group 2 are respectively inoculated into the allantoic cavities of 8-day-old SPF chick embryos at 0.2 ml per embryo. The inoculated chick embryos are cultured in an incubator at 37° C. for 48 h. The chick embryo allantoic fluid (F0-generation) is collected for determining its hemagglutinin titer. F0-generation viruses are diluted and inoculated into 10 SPF chick embryos, cultured for 48 h to obtain viruses which are defined as F1-generation. With the same process, F1-generation viruses are serially passaged to F3-generation.

Results: the detection results are shown in Table 2, from which it can be seen that, for demonstrating whether type B NA gene of different branches can match with H7 subtype HA(H7-BNA) well, NA genes of representative strains from different groups: B/Brisbane/60/2008(Victoria group) and Massachusetts/2/2012(Yamagata group) are selected for study, it is found from the results that type B NA genes of different branches (Victoria group and Yamagata group) both exhibit good matching with H7, the Re-PR8-MuH7-ΔNS vaccine strain obtained from Examples 1 and 3 can approach its upper limit (5 log 2~6 log 2) without the need of passage adaptation on chick embryos. It also can be seen from Table 2 that the growth titers of vaccine strains containing mutant ΔNS are lower than that of wild type by 2 log 2~3 log 2, however, the vaccine strains containing mutant ΔNS are better in terms of safety.

TABLE 2

Growth properties of different chimeric recombinant H7 avian influenza viruses on chick embryos

| Virus | HA Titers (log2) | | | |
|---|---|---|---|---|
| Passage Number | Example 1 Re-Mu1H7-DIVA-ΔNS | Example 3 Re-Mu2H7-DIVA-ΔNS | Control Group 1 PR8-ΔNS | Control Group 2 PR8-WT |
| F0 | 5 | 4 | 6.5 | 9 |
| F1 | 6 | 5 | 7 | 10 |
| F2 | 6 | 5.5 | 7 | 9 |
| F3 | 6 | 5 | 7 | 10 |

For representative influenza B virus strains from different groups: B/Brisbane/60/2008 (Victoria group) and Massachusetts/2/2012 (Yamagata group), the homology between the two NA whole gene nucleotide sequences is 94.9%, the homology of the amino acid sequences is 94.9%; the homology between the two DNA sequences for coding NA protein extracellular region is 95.1%, the homology of the NA protein extracellular region amino acid sequences is 94.6%. Because influenza B is only classified into Victoria group and Yamagata group, it is demonstrated in the invention that representative NA strains from the two groups (Example 1 and Example 3) both have good compatibilities with H7 HA, showing that influenza B virus NA gene may all be used in preparing an H7 avian influenza vaccine strain which differentiates influenza A virus infection from vaccination.

Example 4 Preparation of Re-MuH7-DIVA-ΔNS Inactivated Vaccine 50 ml of F0, F1, F2 or F3-generation allantoic fluids from Re-MuH7-DIVA-ΔNS vaccine strains prepared in the above examples are harvested, and inactivated with a formalin solution at a final concentration of 0.25% at 37° C. for 24 h. The inactivated allantoic fluids are added into 2% of Tween-80, dissolved sufficiently and then emulsified with white oil containing 3% of Span 80 at a proportion of 1:3, at a shear emulsification rate of 12000 rpm for 3 min. Upon a dosage form test, a sizing test, a viscosity test, and a stability test, it is determined that the inactivated vaccine is an off-white water-in-oil emulsion with low viscosity, uniform particle sizes, good stability and suitable for injection.

Example 5 Detection of Effects of Re-MuH7-DIVA-ΔNS Inactivated Vaccine on Vaccinating Animals Process: 10 3-week-old SPF chickens are vaccinated with Re-Mu2H7-DIVA-ΔNS vaccine prepared above at 0.3 ml per chick by subcutaneous injection at the neck, blood is sampled 21 days after vaccination, serum is isolated and HI antibodies are determined.

Results: it is demonstrated from experiments that Re-Mu2H7-DIVA-ΔNS stimulates the organism to generate high level of HI antibodies, the average HI titer (log 2) for week 3 after vaccination is 9.3±0.95. For HA and HI tests, reference to GBT 18936-2003 (diagnosis technology of highly pathogenic avian influenza).

Example 6 Serological Experiments

N1, N2, N6, and N9 genes of the existing influenza A are cloned into pCAGGS eukaryotic expression plasmid through KpnI and NheI sites, which are named as pCAGGS-N1, pCAGGS-N2, pCAGGS-N6, pCAGGS-N9. Each 1 μg of pCAGGS-N1, pCAGGS-N2, pCAGGS-N6, pCAGGS-N9 plasmid is transfected to 293T cells pre-coated on 24-hole cell culture plates. 30 h after transfection, the reactivities of the following 7 groups of chicken serum with N1, N2, N6, N9 are detected by immunofluorescence.

The profiles of the 7 groups of chicken serum are as below:

Anti-Re-Mu2H7-DIVA-ΔNS chicken serum: chicken serum which is only vaccinated with the inventive Re-Mu2H7-DIVA-ΔNS inactivated vaccine;

Anti-H7N9 standard chicken serum: H7N9 standard serum, purchased from Harbin Veterinary Research Institute.

Anti-H5+H7 serum: clinical serum of vaccinated H5N1 Re-8 strain+H7N9 Re-1 strain whole virus inactivated vaccines.

Anti-N1 chicken serum: one-week-old SPF chicken are vaccinated with 100 μg pCAGGS-N1 (by intramuscular injection) respectively, the whole blood is harvested 4 weeks after vaccination to prepare the serum.

Anti-N2 chicken serum: one-week-old SPF chicken are vaccinated with 100 μg pCAGGS-N2 (by intramuscular injection) respectively, the whole blood is harvested 4 weeks after vaccination to prepare the serum.

Anti-N6 chicken serum: one-week-old SPF chicken are vaccinated with 100 μg pCAGGS-N6 (by intramuscular injection) respectively, the whole blood is harvested 4 weeks after vaccination to prepare the serum.

Anti-N9 chicken serum: one-week-old SPF chicken are vaccinated with 100 μg pCAGGS-N9 (by intramuscular injection) respectively, the whole blood is harvested 4 weeks after vaccination to prepare the serum.

The immunofluorescence process is as below:

1) Into each cell is added 0.5 ml of 4% paraformaldehyde for immobilization for 20 minutes, and then washed with PBS for three times.

2) It is permeated with 0.2% Triton X 100 for 10 minutes, and then washed with PBS for three times.

3) It is blocked with 5% BSA for 1 hour, and then washed with PBS for three times.

4) Primary antibodies are diluted with PBS containing 1% BSA by corresponding factors (anti-Re-Mu2H7-DIVA-ΔNS, anti-H7N9 standard, anti-H5+H7, for 100-fold; anti-N1/N2/N6/N9, for 20-fold), and added into each hole at 0.5 ml, incubated in a wet box at 37° C. for 1 hour, and then washed with PBS for three times.

5) Anti-Chicken secondary antibodies (Alexa Fluor 594 Donkey Anti-Chicken IgY) are diluted with PBS containing 1% BSA for 200-fold, added into each hole at 0.5 ml, incubated at room temperature for 0.5 hours, and then washed with PBS for three times.

6) Observing with a fluorescence microscope.

Figure 3:
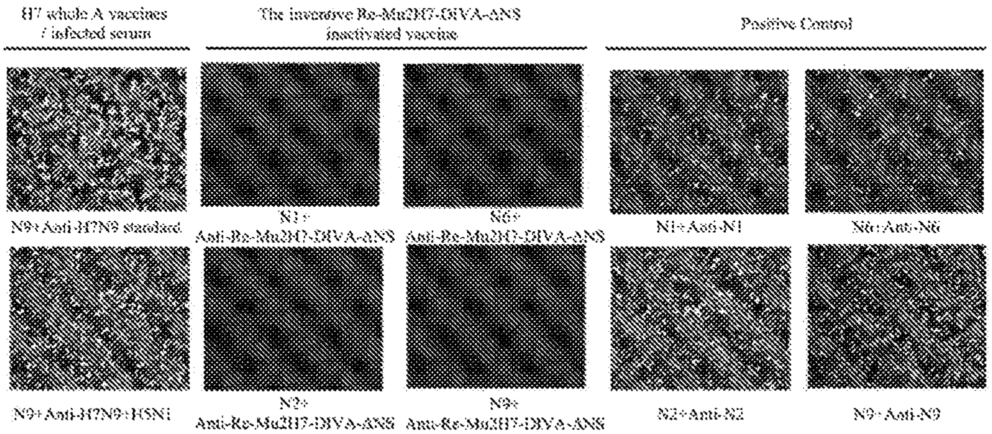
FIG. 3 is detecting the reactivity of anti-Re-Mu2H7-DIVA-ΔNS serum with influenza ANA by immunofluorescence.

Results: Influenza N1, N2, N6 and N9 neuraminidases are respectively expressed in 293T cells, the immunofluorescence process is used to detect whether serum has reacted with N1, N2, N6 and N9 3 weeks after vaccination with Re-Mu2H7-DIVA-ΔNS. It is found that the anti-Re-Mu2H7-DIVA-ΔNS serum does not cross react with N1, N2, N6 and N9 proteins (e.g., as shown in Table 3 and FIG. 3), both clinical serum vaccinated with the existing whole type A virus vaccines (H5N1 Re-8 strain+H7N9 Re-1 strain) and anti-H7N9 standard serum can strongly react with N9 protein. It is demonstrated from this experiment that vaccination with the Re-Mu2H7-DIVA-ΔNS vaccine can not only induce high level of HI antibodies, but also can differentiate infected from vaccinated animals, which overcomes the disadvantage that the existing H7 subtype whole virus vaccine is unable to differentiate infected from vaccinated animals.

TABLE 3

The reactivity profiles between chicken sera vaccinated with different antigens and each NA subtype

| Antibodies | HI | Antigens | | | |
|---|---|---|---|---|---|
| | | N1 | N2 | N6 | N9 |
| Anti-Re-Mu2H7-DIVA-ΔNS | HI: 9 log2 | No reactivity | No reactivity | No reactivity | No reactivity |
| Anti-H7N9 standard | HI: 8 log2 | ND | ND | ND | Reactivity |
| Anti-H5 + H7 | HI: 9 log2 (H7) | ND | ND | ND | Reactivity |
| Anti-N1 | HI: N/A | Reactivity | ND | ND | ND |
| Anti-N2 | HI: N/A | ND | Reactivity | ND | ND |
| Anti-N6 | HI: N/A | ND | ND | Reactivity | ND |
| Anti-N9 | HI: N/A | ND | ND | ND | Reactivity |

Note:
N/A: not applicable; ND: not detected.

Example 7 A Preparation Method of an H7 Avian Influenza Vaccine Strain Re-MuH7-DIVA-ΔNS which Differentiates Influenza A Virus Infection from Vaccination The preparation method of Example 7 is the same as that of Example 1, except that in constructing the artificially synthesized A/B chimeric NA gene as shown in FIG. 1, the influenza B virus NA sequence used is the DNA sequence for coding NA whole protein sequence, the remaining are all the same as Example 1, wherein, the DNA sequence of NA derived from the NA whole gene sequence of B/Massachusetts/2/2012 in the Yamagata group of influenza B virus (Ping J et al, PNAS, 2016, 113(51): E8296-E8305).

The above examples are the preferable embodiments of the invention, however, the detailed description of the invention is not limited to the examples described above, any other changes, modifications, substitutions, combinations, simplifications made without deviating from the spirit and principle of the invention should all be considered as equivalent replacements, which are all within the scope of the present invention.

What is claimed is:

1. An H7 avian influenza vaccine comprising an H7 avian influenza virus with a label gene sequence selected from the group consisting of: the label gene sequence containing a DNA sequence for coding an influenza B virus Neuraminidase (NA) protein extracellular region amino acid sequence, or containing a DNA sequence for coding an amino acid sequence having at least 90% identity, or at least 92% identity, or at least 95% identity, or at least 98% identity with the extracellular region amino acid sequence;

alternatively, the label gene sequence containing a DNA sequence for coding the extracellular region amino acid sequence in influenza B virus NA gene, or containing a sequence having at least 90% identity, or at least 92% identity, or at least 95% identity, or at least 98% identity with the DNA sequence;

alternatively, the label gene sequence is a DNA sequence for coding influenza B virus NA protein, or a DNA sequence for coding an amino acid sequence having at least 90% identity, or at least 92% identity, or at least 95% identity, or at least 98% identity with the NA protein amino acid sequence; and alternatively, the label gene sequence is a DNA sequence of influenza B virus NA gene, or a sequence having at least 90% identity, or at least 92% identity, or at least 95% identity, or at least 98% identity with the DNA sequence;

wherein the H7 avian influenza vaccine strain further contains an H7 subtype hemagglutinin (HA) gene encoding VPKGKRTARGLF (SEQ ID NO: 8) or a mutated H7 subtype HA gene; wherein the mutated H7 subtype HA gene has been mutated to encode VPSSRSRGLF (SEQ ID NO: 9) or VPKGRGLF (SEQ ID NO: 10) in place of VPKGKRTARGLF (SEQ ID NO: 8).

2. The H7 avian influenza virus of claim 1, wherein the influenza B virus NA is from influenza B viruses of Victoria group or Yamagata group.

3. The H7 avian influenza virus of claim 2, wherein the influenza B viruses are strains B/Massachusetts/2/2012, B/Brisbane/60/2008, B/Yamagata/16/1988 or B/Malaysia/2506/04.

4. The H7 avian influenza virus of claim 1, wherein the label gene sequence further contains packaging signal sequences at its both ends, the packaging signal is a packaging signal of H1 subtype NA, or a packaging signal sequence having at least 80% identity, or at least 85% identity, or at least 90% identity, or at least 95% identity with the packaging signal of H1 subtype NA.

5. The H7 avian influenza virus of claim 1, wherein the label gene sequence further contains packaging signal sequences at its both ends, wherein the 5'-end packaging signal sequence comprises the noncoding region sequence, the intracellular region sequence, and the transmembrane region sequence of H1 subtype NA.

6. The H7 avian influenza virus of claim 5, wherein the intracellular region sequence encodes 5 to 7 amino acids.

7. The H7 avian influenza virus of claim 5, wherein the transmembrane region sequence encodes 24 to 32 amino acids.

8. The H7 avian influenza virus of claim 5, wherein the 5'-end packaging signal sequence of the label gene sequence is SEQ ID NO:3, or a sequence having at least 80% identity, or at least 85% identity, or at least 90% identity, or at least 95% identity with SEQ ID NO:3.

9. The H7 avian influenza virus of claim 1, wherein the label gene sequence further contains packaging signal sequences at its both ends, wherein the 3'-end packaging signal sequence is SEQ ID NO:4, or a sequence having at least 80% identity, or at least 85% identity, or at least 90% identity, or at least 95% identity with SEQ ID NO:4.

* * * * *